(12) United States Patent
Okada

(10) Patent No.: US 8,527,029 B2
(45) Date of Patent: Sep. 3, 2013

(54) MODULAR ARRAYS OF PRIMARY SOURCE MIRRORS FOR BIOMAGNETOMETRY

(75) Inventor: Yoshio Okada, Boston, MA (US)

(73) Assignee: Moment Technologies, LLC, Boston, MA (US)

( * ) Notice: Subject to any disclaimer, the term of this patent is extended or adjusted under 35 U.S.C. 154(b) by 140 days.

(21) Appl. No.: 13/206,392

(22) Filed: Aug. 9, 2011

(65) Prior Publication Data

US 2013/0038325 A1 Feb. 14, 2013

(51) Int. Cl.
*A61B 5/05* (2006.01)

(52) U.S. Cl.
USPC .......................................... 600/409; 600/407

(58) Field of Classification Search
USPC .................. 600/409; 324/244, 245, 246, 226
See application file for complete search history.

(56) References Cited

U.S. PATENT DOCUMENTS

| | | |
|---|---|---|
| 5,938,598 A | 8/1999 | Takeda et al. |
| 6,226,538 B1 | 5/2001 | Kugai et al. |
| 6,815,949 B2 | 11/2004 | Kandori et al. |
| 7,002,341 B2 | 2/2006 | Baudenbacher et al. |
| 7,197,652 B2 | 3/2007 | Gott et al. |
| 7,262,597 B2 | 8/2007 | Woods et al. |
| 7,403,809 B2 | 7/2008 | Tsukada et al. |
| 7,672,707 B2 | 3/2010 | Takeda |

*Primary Examiner* — Unsu Jung
*Assistant Examiner* — Rajeev Siripurapu
(74) *Attorney, Agent, or Firm* — The Maxham Firm

(57) ABSTRACT

Apparatus and methods enabling the improved noninvasive measurement of electric currents flowing in the body of a human being or animal or in a biological sample by way of a modular array of primary source mirrors and a magnetometer.

26 Claims, 8 Drawing Sheets

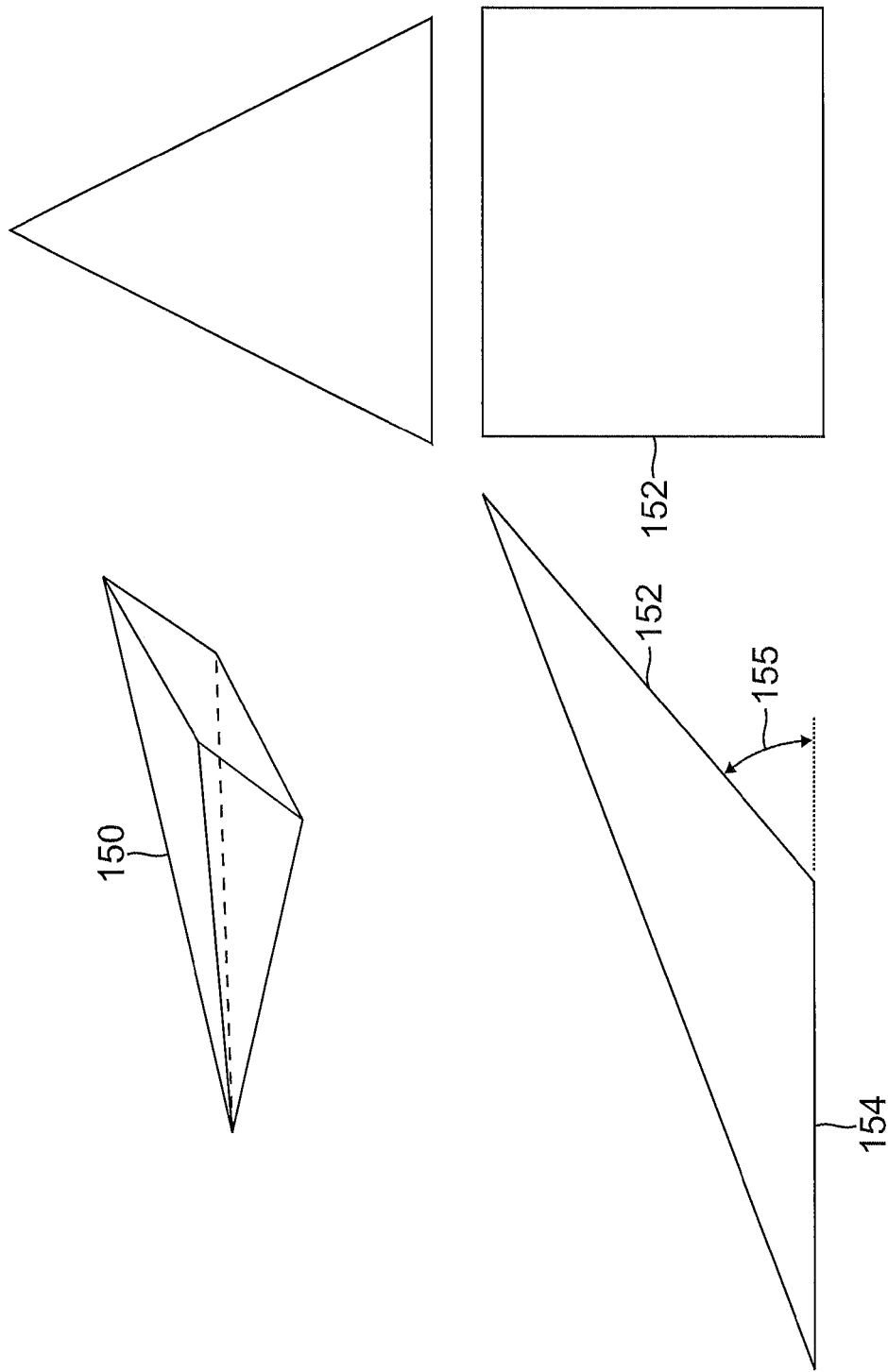

MODULAR ARRAYS OF PRIMARY SOURCE MIRRORS FOR BIOMAGNETOMETRY

FIELD OF INVENTION

The present application relates generally to the field of measuring the magnetic fields produced by naturally occurring electric currents which flow in the body of a human being or animal, and more particularly to apparatus and methods for making such measurements.

BACKGROUND OF THE INVENTION

The term biomagnetometry refers to the detection and measurement of magnetic fields produced by biologic organisms and samples of tissue taken from such organisms. One specialty within the general field of biomagnetometry is magnetoencephalography (often abbreviated by the acronym "MEG"). MEG refers to the detection and measurement of the magnetic fields which are produced by the electric currents which flow naturally within the bodies of humans and animals. For example, such electric current flows are a fundamental feature of the functioning of the neurological system of a human being. Charged ionic flow within the neurons which make up part of the human brain and nervous system is, in effect, an electric current which produces a magnetic field which can be measured using the methods of MEG. The electric currents which drive the pumping of the heart in an animal produce magnetic fields which can be measured using magnetocardiography. Measurements of the magnetic fields produced by these electric currents can be used to deduce information about the size and direction of the currents as a function of time as well as their location and distribution within the body of a person, and therefore to provide information about the state of health and the state of function of the person.

Apparatus and methods of MEG have been developed and expanded over the past forty years, enhancing sensitivity to enable the detection of magnetic fields produced by electric currents flowing deep within the body. The "field of view" of the magnetometers used for MEG has been systematically expanded from single channel detectors of the magnetic field at one location to large helmet-shaped systems measuring the values of the magnetic fields at up to 275 locations around the head of a human being or up to 150 locations over the chest of a human being.

Generally, the biomagnetic measurements of biogenic electric currents are useful for measuring the distribution of such currents in an organ such as a brain or heart. However, one major limitation in the application of the biomagnetic techniques for the purposes outlined above arises from a fundamental property of magnetic fields produced by electric currents flowing in such organs within the body of a human or animal. Any such organs can be described by a circuit of electrically active cells that produce the biogenic current. In intact humans or animals, the tissue of the organ that contains such electrogenic cells is saturated with physiological saline. The physiological saline conducts electricity; thus, the medium containing the saline such as the brain or the head is called a "conductive medium." The term "conductive" in the context of the current invention refers to the physical property of "electrical conductivity," and all use of the term "conductive" hereafter will mean "electrically conductive." From the fundamental principles governing electromagnetism in conductive media, an electric current which flows within and proximate to the surface of such a conductive medium and which flows in a direction which is perpendicular to the surface of that medium produces no net magnetic field external to the medium itself. This is strictly true when the surface boundary between the conducting medium and a non-conducting medium (such as air) is spherical or flat. This factor has limited the utility of biomagnetic measurements such as MEG in providing complete information about electric currents in a tissue or in an organ. The conventional biomagnetic techniques can provide the information only about those components of the electric currents flowing within conducting media which flow in a direction parallel to the surface of that medium, but not the currents which flow normal to the surface. This factor has significantly constrained the application of the biomagnetic techniques for measuring biogenic currents from human and animal brains.

Apparatus and methods for removing this limitation is the field of biomagnetic measurement has been recently developed and has been disclosed in a patent application submitted to the U.S. Patent and Trademark Office on 3 Mar. 2011 and assigned application Ser. No. 13/040,027. This apparatus requires the placement of a non-conducting object known as a primary source mirror (hereinafter PRISM), within a conducting medium in close proximity to the electric currents of interest as they flow within the human or animal body. As noted above, magnetometers for performing MEG are now available which enable the concurrent measurement of the magnetic fields at hundreds of locations on the surface of a human head or elsewhere on the surface of the human body or in a tissue sample for in vitro measurements. However, the limitation of only being able to record the magnetic fields produced by electrical currents flowing in a direction parallel to the surface near the region of interest remains with such large measurement apparatus. This limitation can be removed by use of the basic method of a single primary source mirror as disclosed in the patent application cited above in an expanded manner employing large numbers of such mirrors concurrently.

The use of large arrays of primary source mirrors concurrently for this purpose requires the placement of a conductive medium over the surface of the biological preparation in the region of interest and the placement of such mirrors within this medium and close to the locations of the electrical currents which are of interest. Since these locations are generally not known prior to measurement, it is desirable to place a large number of mirrors immersed in conductive media over the large portion of entire surface of the biological preparation. By doing so, a magnetometer measuring the magnetic fields at hundreds of locations over the surface will measure both the currents flowing parallel to the boundary surface of the conducting medium containing the sample (such as the air-head surface of the head containing the brain) and those flowing perpendicular to such a surface, and thus by vector addition, will measure the magnetic fields coming from electric currents flowing in any direction relative to the surface. Thus, the use of primary source mirrors enables the complete characterization of the biological currents.

The placement of a conductive medium over the boundary surface of the conducting medium (such as the human head or chest) and the immersion of hundreds of primary source mirrors within that medium is a difficult process and one which takes a great deal of time and a great deal of painstaking work to ensure that each mirror is properly oriented and properly fixed in position. There is no known means for performing this task efficiently and effectively if the potential of this method is to be practically realized for all types of biological samples including application to the brain and other organs of a human being or animal, to the neurological system of humans or animals in situ, to tissue samples in a variety of in vitro configurations, and similar types of electrophysiological recording requirements.

SUMMARY OF EMBODIMENTS OF THE INVENTION

Embodiments of the present invention relate to a novel use of the PRISM technology described above for measuring biomagnetic fields. In its basic form, a single PRISM is placed in a conducting medium that contains a biological tissue or an organ. In the current invention, a number of PRISMs are assembled as a module and these modules are combined into an array which can take a variety of geometric forms. Each module contains the conductive medium which enables operation of the PRISM method. The array of modules is placed over the biological preparation such as a tissue sample or a human or animal body. This enables non-invasive measurements of the biomagnetic signals within a human or animal body or a tissue. Moreover, the use of the array enables measurements of the biomagnetic signals simultaneously over the entire preparation such as a tissue, an intact heart or head, using a multichannel biomagnetometer. This second feature is significant as well since biological events are often not repeatable and thus they must be captured instantaneously.

The following summary of embodiments of the invention is provided to enable an understanding of some of its novel features but is not intended to be a full description. A full appreciation of the aspects of the various embodiments will be provided by the specification, claims, drawings, and abstract as a whole.

Accordingly, it is a purpose of embodiments of the present invention to provide apparatus and methods for enabling the construction of a PRISM array and the efficient placement of a conductive medium over a biological sample (such as selected portions of the surface of the body of a human being or an animal) and the placement of the desired number of primary source mirrors within that conductive medium at the desired locations and with the desired orientations. This enables the detection and assessment of all components of the biogenic currents, including those currents flowing in a direction perpendicular to the boundary surface (such as surface of the human body), by means of a biomagnetometer placed over the array of primary source mirrors. The use of these embodiments will therefore enable a more complete assessment of all components of electric currents which flow within a biological sample such as the body of a human being or animal.

One feature of the invention is to provide a structure which provides a plurality of primary source mirrors or PRISMs assembled as single modules. Each PRISM perturbs the electric current that flows in the conducting medium when neuronal structures are electrical active and produce so-called primary currents. The perturbation of the electric currents produces so-called secondary sources of magnetic fields induced by primary electric currents flowing in the biological sample. Detection and measurement of the magnetic fields produced by the secondary sources will provide information about the size and location of the components of the primary electric currents that are oriented perpendicular to the boundary surface of the sample. Secondary sources in general exist at boundary surfaces separating regions differing in electrical conductivity. Secondary sources generate magnetic fields that are directly related to the currents in the primary source. Thus, it is possible to indirectly measure the primary currents flowing perpendicular to the boundary surface which are otherwise not detectable with conventional biomagnetometry.

Another feature of the invention is to provide a unitary apparatus which provides a plurality of secondary sources and a conductive medium in a modular form which can easily be placed over areas of the surface of a human or animal body in a variety of configurations.

A further feature of the invention is to provide a plurality of modules assembled as arrays, each of which provides a plurality of secondary sources of magnetic fields induced by primary currents flowing in a human or animal body or other biological preparation, and to provide means to configure the plurality of modules to conform closely to selected regions of the biological preparation to be tested.

A still further feature of the invention is to provide an apparatus and method which enables an expanded capability to perform functional assessments of the electrophysiological structures of human beings or animals by means of biomagnetic measurements.

BRIEF DESCRIPTION OF THE DRAWING

The objects, advantages, features, and other desirable characteristics of embodiments of the invention can be readily perceived from the following detailed description and attached drawing, in which:

FIGS. 3a, 3b, 3c, and 3d are drawings showing several views of each of four forms of primary source mirrors suitable for use in embodiments of the invention;

DETAILED DESCRIPTION OF EMBODIMENTS OF THE INVENTION

As noted above, it is a fundamental property of the physics of electromagnetism that, at the boundary between a conductive medium and a non-conductive medium, an electric current which is flowing within the conductive medium and in a direction parallel to the boundary produces a magnetic field that extends throughout both the conductive and non-conductive media. However, an electric current which is flowing within the conductive medium and in a direction orthogonal to the boundary produces a magnetic field which extends throughout the conductive medium but produces no magnetic field in the non-conductive medium. This is strictly true for a conducting medium having a spherical symmetry such a sphere, or a semi-infinite planar structure. The human head is nearly spherical, at least over a large dorsal portion of the head. The region of the chest or back close to the heart of a human being is nearly planar and well approximated as a semi-infinite planar conductive medium. In these cases, the approximation is excellent. (See F. Grynszpan and D. B. Geselowitz, Biophysics Journal, Vol. 13, pp. 911-925 (1973); also D. Cohen and H. Hosaka, *J. Electrocardiol.*, 1976, Vol. 9, pp. 409-417 (1976); also Y. C. Okada and C. Nicholson, *Biophys. J.*, Vol. 53, pp. 723-731 (1988)).

One effective means for determining the characteristics of an electric current flowing in a conductive medium—location, amplitude, and direction of flow—as a function of time is by measuring the magnetic field produced by that current. However, because magnetic fields external to the conductive medium are only produced by those currents which flow in a direction parallel to the surface or boundary of the medium, this method is severely limited. Placing a magnetic field detector within the conductive medium itself is a potential approach but faces numerous practical difficulties. Placing a magnetic field detector external to the conductive medium limits this method to determining the characteristics only for the electric current components which are parallel to the surface of the medium. The invention of a primary source mirror or PRISM disclosed in patent application Ser. No. 13/040,027 provided a method for countering this limitation. However, the method disclosed therein is typically invasive, requiring the placement of a non-conducting object within the conductive medium containing the electrophysiological current of interest.

Figure 1:
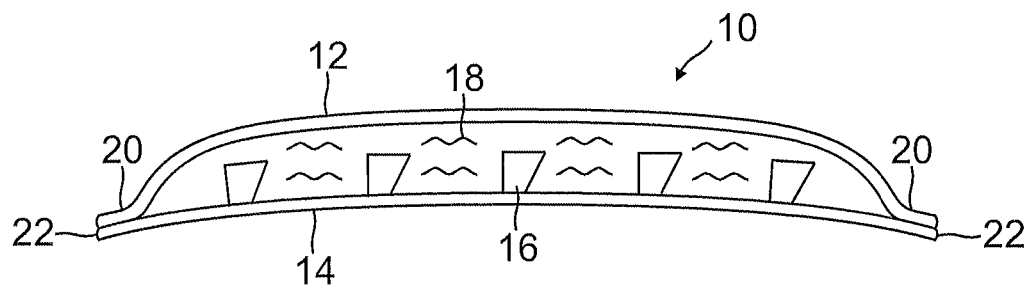
FIG. 1 is a cross-sectional view of a primary source mirror module containing a number of primary source mirrors or PRISMs.

Embodiments of the current invention are aimed at alleviating the limitation of the disclosed method of application of the PRISM technology by methods that are totally noninvasive, and thus aimed at applications where noninvasive measurements of biological signals are necessary. Moreover, all embodiments of the current invention are focused on enabling simultaneous measurements of the biomagnetic signals over the entire preparation, which are critical for those applications in which events can not be easily repeated and reproduced. FIG. 1 shows a preferred embodiment of the basic element of the invention comprising a primary source mirror array placed inside a modular housing or module 10. The module is comprised of an electrically conductive wall 14 and a non-electrically conductive wall 12. The two walls are flexible and curved to form an envelope joined in a planar manner to each other around the periphery of the envelope at seal 20. The attachment of walls 12 and 14 to each other as well as the formation of seal 20 is undertaken using a suitable adhesive. Typical adhesives are rubber cement, two-part epoxy, or silicone sealant/adhesives. The envelope is filled with an electrically conductive gel 18. An example of a suitable gel is that which is used to attach electrocardiography (EKG) electrodes to the body of a patient undergoing an EKG examination. Within the envelope and mounted on electrically conductive wall 14 and immersed in the gel is an array of primary source mirrors (PRISMs) 16, spaced apart and geometrically oriented to provide secondary sources of magnetic fields produced by primary magnetic sources located external to the envelope and adjacent to conductive wall 14. The module is also provided with a flange 22 around its periphery which enables multiple modules of similar structure to be attached together.

Figure 2:
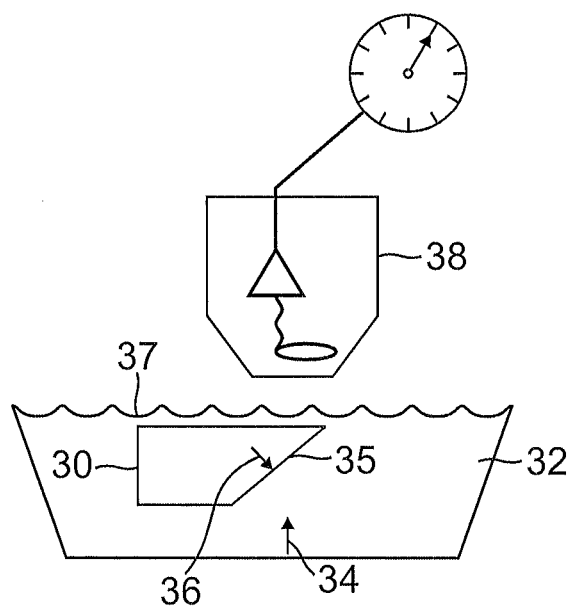
FIG. 2 is a drawing showing the principal of operation of a single primary source minor.

FIG. 2 illustrates the fundamental principle of operation of a primary source mirror or PRISM. A solid object 30 made from a non-conductive material is fully immersed in conductive medium 32. Examples of a conductive media are saline solution, conductive gel as used in electroencephalography recordings or, in the human body, cerebrospinal fluid. Examples of a suitable non-conductive material are glass or plastic resin. Positioned above the conductive medium and solid object 30 is sensor 38 which can measure the magnetic field at the location of the sensor. An example of such a sensor is a magnetometer such as a flux-gate magnetometer or a superconducting magnetometer utilizing superconducting quantum interference devices (SQUIDs). Solid object 30 has at least one flat surface 35 and the object is positioned so that the flat surface is at an approximately 45 degree angle to surface 37 of the conductive medium located between the object and the sensor as shown. Located within conductive medium 32 and below solid object 30 near flat face 35 is a primary electrical current element called a primary current dipole 34 which has a direction vector orthogonal to the plane of the surface 37 of the conductive medium between the object and the sensor. The electrical current which makes up the primary current dipole is thus flowing in a direction perpendicular to the nearby surface of the conductive medium and, as noted above, will therefore produce no net magnetic field external to the conductive medium. Sensor 38 detects no magnetic field coming directly from that primary current source. However, according to the theory of secondary magnetic sources in electrically conductive and non-conductive media, a secondary source of magnetic field 36 is induced on flat surface 35 of solid object 30. (See, for example, R. Plonsey in *Biomagnetism*, Berlin, De Gruyter, pp. 177-205 (1981)). This secondary source is equivalent to a current dipole oriented perpendicular to flat surface 35. Because flat surface 35 is oriented at a 45 degree angle to surface 37 of the conductive medium, this secondary current dipole source will have a component which is oriented parallel to conductive medium surface 37 and will produce a magnetic field external to the conductive medium which can be measured by the sensor 38. In this manner, primary source mirror 30 enables the detection and measurement of electrical currents flowing in the conductive medium which would otherwise be undetectable externally to the medium using a sensor such as 38.

Figure 3A:
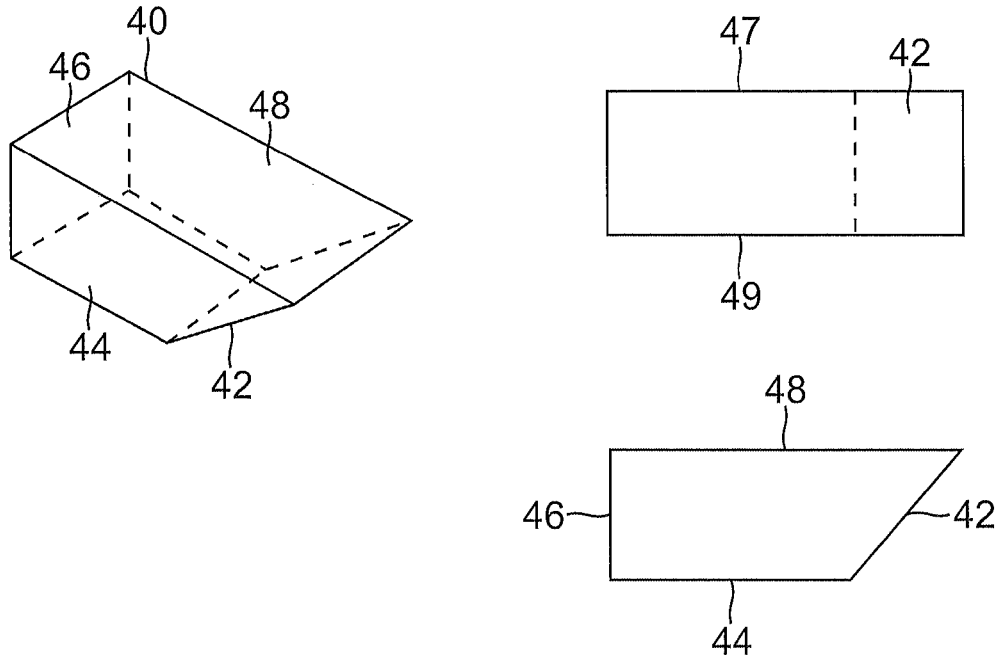

FIG. 3a shows one example of a primary source mirror or PRISM which can be used to construct the array shown in FIG. 1. With reference to the three views of the PRISM shown, PRISM 40 is a hexahedron which has the form of a rectangular non-conductive solid having flat faces on all sides which are either parallel or orthogonal to each of the other faces, except side 42 which is at an acute angle relative to side 48. In a preferred embodiment, side 42 is at an angle of 45 degrees from side 48 and orthogonal to sides 44 and 47. A preferred material for the non-conductive solid is glass. Alternative materials from which the non-conductive solid can be fabricated include, but are not limited to, sapphire, quartz, diamond, and filled composite plastics.

Figure 3B:
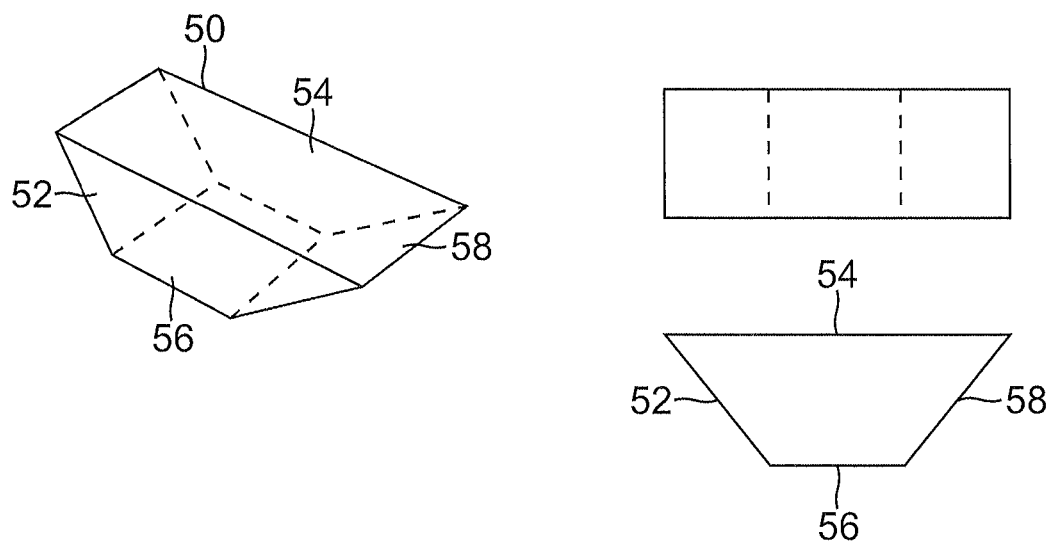

Shown in FIG. 3b is PRISM 52, having a geometry that is different from PRISM 40. This example is also a hexahedron if the form of a rectangular solid similar to PRISM 40 but has two flat surfaces 52 and 58, each at an acute angle relative to surface 54. Secondary sources can then be induced in both sides 52 and 58 by one or more primary sources adjacent to side 56.

Figure 3C:
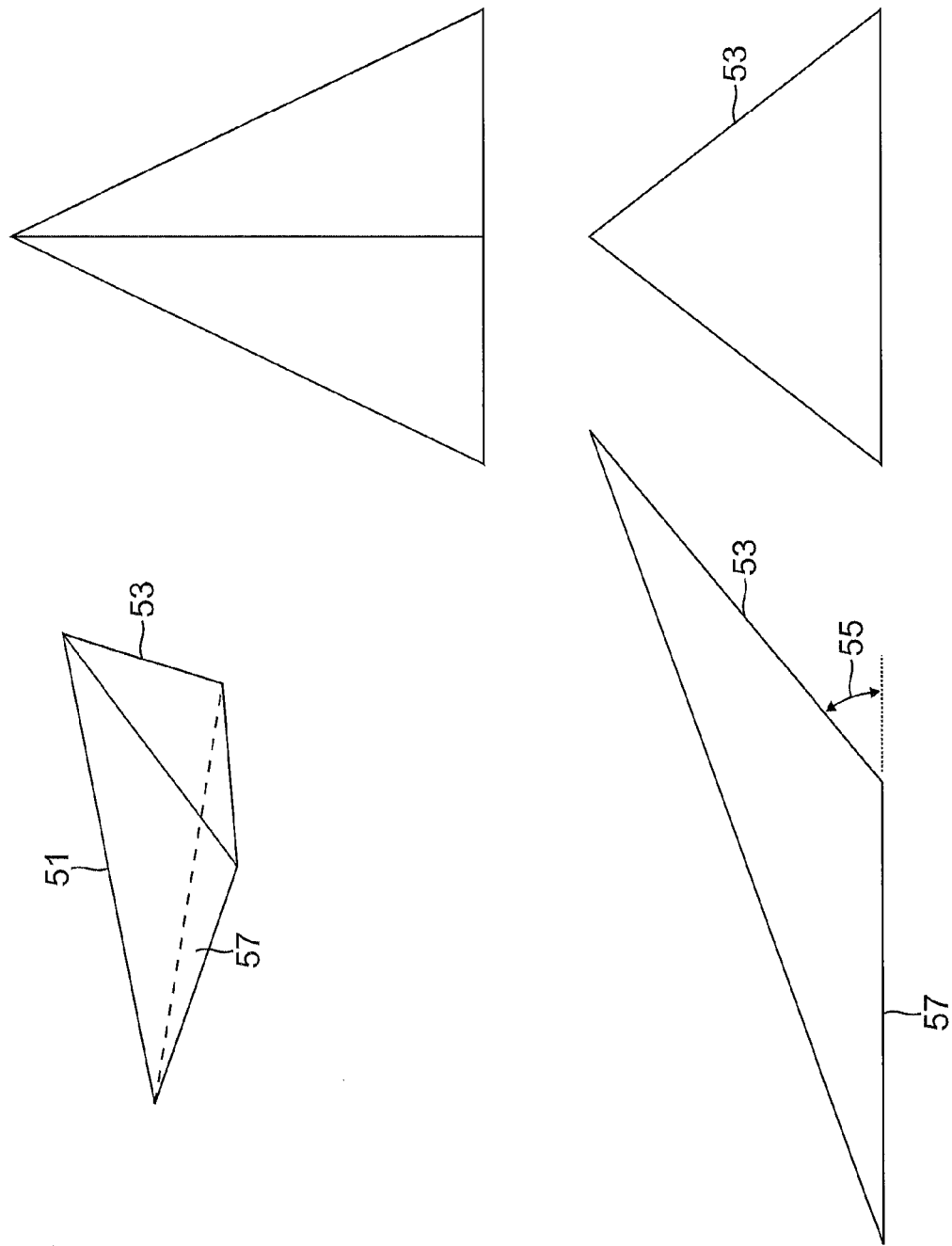

Shown in FIG. 3c is a third example of a PRISM. In this example, PRISM 51 is a tetrahedron with one triangular face 53 which lies at an acute angle 55 with respect to the plane of face 57. Face 57 would be placed against conductive surface 14 of module 10 in FIG. 1. Secondary sources can then be induced in face 53 by nearby primary sources lying below face 53. A preferred value for angle 55 is 45 degrees.

Shown in FIG. 3d is a fourth example of a PRISM. PRISM 150 is an example of a pentahedron with one rectangular face 152 which lies at an acute angle 155 with respect to the plane of face 154. Face 154 is adapted to be placed against the conductive surface 14 of module 10 in FIG. 1. Secondary sources can then be induced in face 154 by nearby primary sources lying below face 154. A preferred value for angle 155 is 45 degrees.

Many other geometric configurations may be chosen for the PRISMs installed in the modules. The four PRISMs shown in FIGS. 3a, 3b, 3c, and 3d are preferred embodiments of PRISMs because of their relatively simple geometry and suitability for robust and efficient attachment to surface 14 of module 10. Typical dimensions for such PRISMs will be 0.1 mm to 10 mm on a side, depending on application. The use of multiple PRISMs of this size located close to each other can provide spatial resolution for current source localization of 0.1 mm to 10 mm or better.

The physical dimensions of surfaces 12 and 14 of module 10 are chosen depending on the curvature of the sample against which the module will be placed in use. More sharply curved shapes, such as the more curved portions of a small head, would require smaller module sizes to enable assembling a larger number of them together into a curved shape to cover the region of the head of interest. Flatter shapes, such as the chest of a person for which measuring the electrical currents flowing in the heart is of interest, would allow for larger module dimensions. A completely flat small module will be for a biological or any other conductive sample in which there is a distribution of currents. Typically for modules to be used on the head, module lengths and widths of two to three centimeters are best. For modules to be used on chest, module lengths and widths of seven to eight centimeters may be selected. For modules to be used on biological samples such as a tissue containing neurons, the dimensions may be a few millimeters on each side. In all cases, the thickness of each module is typically selected to be only minimally greater than the thickness of the PRISMs being employed. This provides compactness and flexibility and also minimizes the spacing between a magnetic sensor and the sample.

Conductive wall 14 (FIG. 1) is preferred to have an electrical conductivity close to that of the sample containing the primary source currents. A preferred wall material is a semipermeable membrane which becomes permeated by electrically conductive gel 18. Alternatively, a cloth screen with very fine hole sizes (similar to that used in water filtering processes) may be used and impregnated with the electrically conductive gel. The number of PRISMs installed as a PRISM array in module 10 is selected based on the size of the module but spacing between PRISMs within a module is minimized to increase spatial resolution for primary current sources. For measurements of a human head, a spacing of 5-7 millimeters between adjacent PRISMs is optimal in view of the thickness of the human skull. For use with very young children or neonates, closer spacing is preferred owing to the thinner, lesser developed skulls of these persons. The spacing may be on the order of a few millimeters for biological tissue samples.

One method for fabricating module 10 having a very large number of PRISMs attached to the interior surface of conducting wall 14 with the locations of each PRISM precisely controlled and known uses the methods of stereo lithography. In this method, the array of PRISMs is effectively printed layer-by-layer onto the conductive surface. One suitable material which may be used in this process is plastic resin. This fabrication method would also permit a variety of PRISM geometries such as those shown by example in FIGS. 3a, 3b, 3c, and 3d to be used with each individual PRISM selected to have an optimal geometry in view of its position within the module.

Figure 4A:
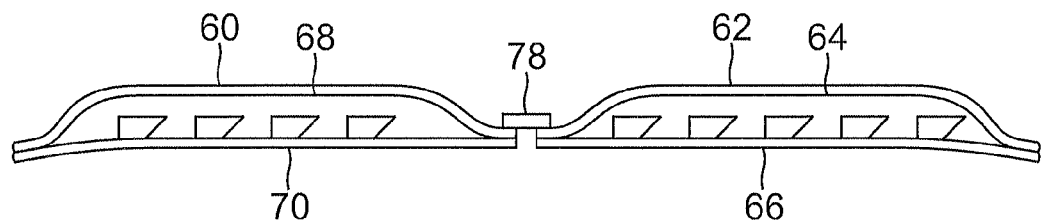
FIGS. 4a, 4b, and 4c show two primary source mirror modules joined along one common edge to form an array.

FIG. 4 shows two modules 60 and 62 attached together along one edge of each module. It is not necessary to have the conductive walls of adjacent modular housing be in electrical contact with each other, and incidental contact should not adversely affect performance of the PRISMs in each module. The flanges on modules 60 and 62 are extensions of module walls 68, 70, and 64, 66. Alternatively, the flanges can be formed of only extensions of conductive walls 70 and 66. Attachment of the flanges can be effected through the use of strip 78, as shown in FIG. 4a. The strip may be made from a flexible material which is wide enough to cover both flanges and is secured to both using an adhesive such as two-part epoxy, cyanoacrylate adhesive, or another suitable adhesive. For example, strip 78 may be made of the same material used for the conductive or non-conductive walls of the modules, although it is preferable to select a material which offers greater flexibility and strength to prevent deterioration of the attachment after repeated flexing in use.

Figure 4B:
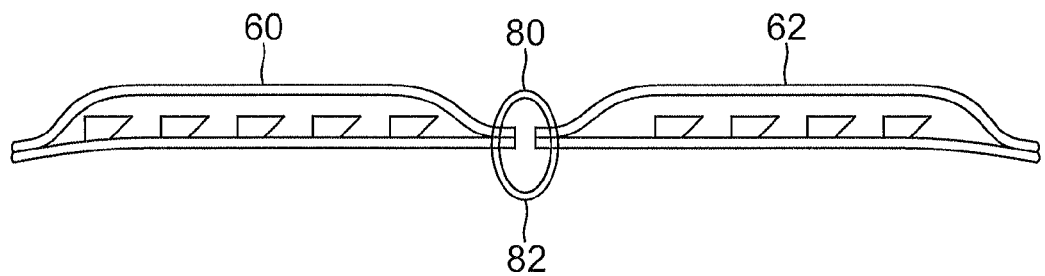
Figure 4C:
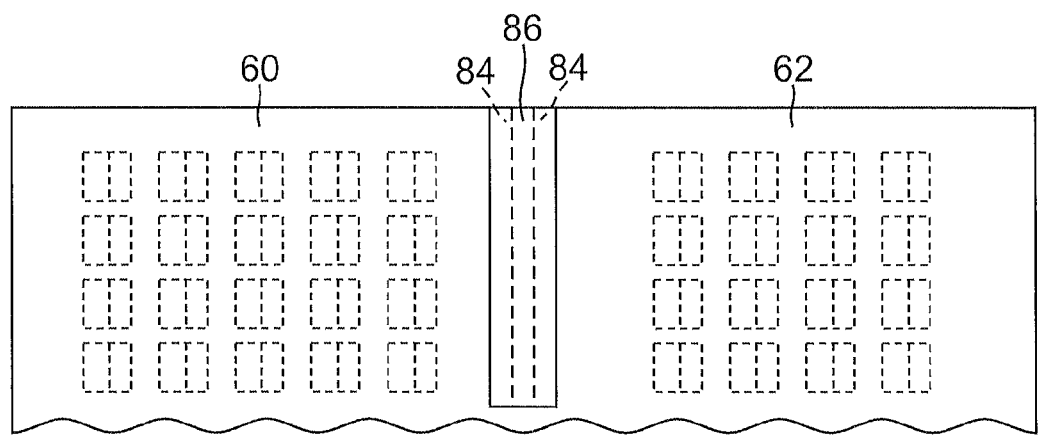

Alternatively, FIG. 4b also shows how the flanges can be stitched together using nylon or similar thread 82. A series of holes can be provided in the flanges of the modules to permit the passage of loops of thread 80 to effect the stitching. A third alternative means of attaching the flanges together is to use a hook and loop fastener strip, as shown in FIG. 4c. A strip of hooks 84 is attached with adhesive to the each flange on each module and a strip of loops 86 is attached to a strip of material with sufficient width to span the two flanges and engage to strips of hooks to attach two modules together. With this method, the attachment can be made and unmade quickly as needed by the application at hand.

In a similar manner, large numbers of module can be attached edge-to-edge. For example, arrays comprising two or more rectangular modules in one direction and two or more rectangular modules in another direction can be constructed. Attachment of the flanges of adjacent modules can be effected on one, two, three, or all four edges of each module as required to build the desired array.

The plan-view shape of the conductive and non-conductive walls of the modules shown in FIG. 4c has been shown to be rectangular for illustrative purposes. However, module walls may be constructed in any desired shape. A combination of rectangular shapes, triangular shapes, and other polygonal shapes may be selected and attached using the methods described above to form an array which conforms optimally to the shape of the sample containing the currents of interest, such as a heart or brain.

Figure 5:
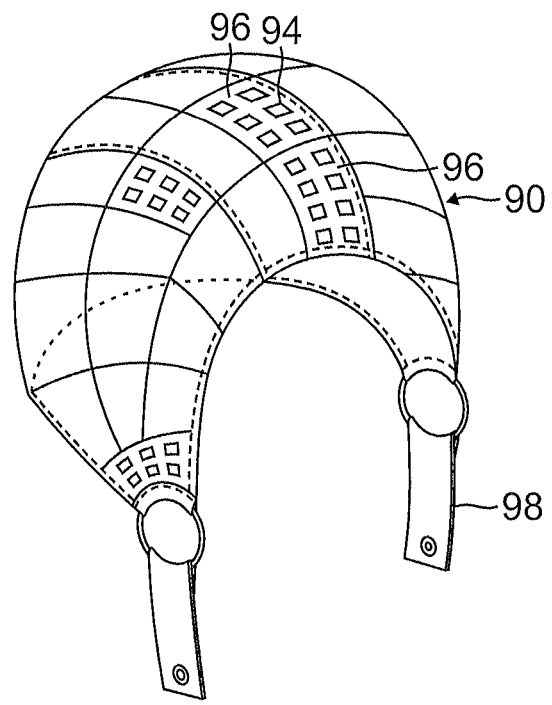
FIG. 5 shows a number of primary source mirror modules attached together to form a cap shape which conforms to the head of a human being.

FIG. 5 shows a specific embodiment 90 of a PRISM module array which has been constructed from a number of PRISM modules 94 in the form of a cap which will fit closely over the skull of a human head. The flanges of each module 96 are attached to the flanges of all adjacent modules. The modules may have trapezoidal shapes or hexagonal shapes to make up the overall shape of a cap sized to fit the head. The cap is provided with chin strap 98 to secure it to the head of a person, with the chin strap attached to modules using methods similar to those described above.

Figure 6:
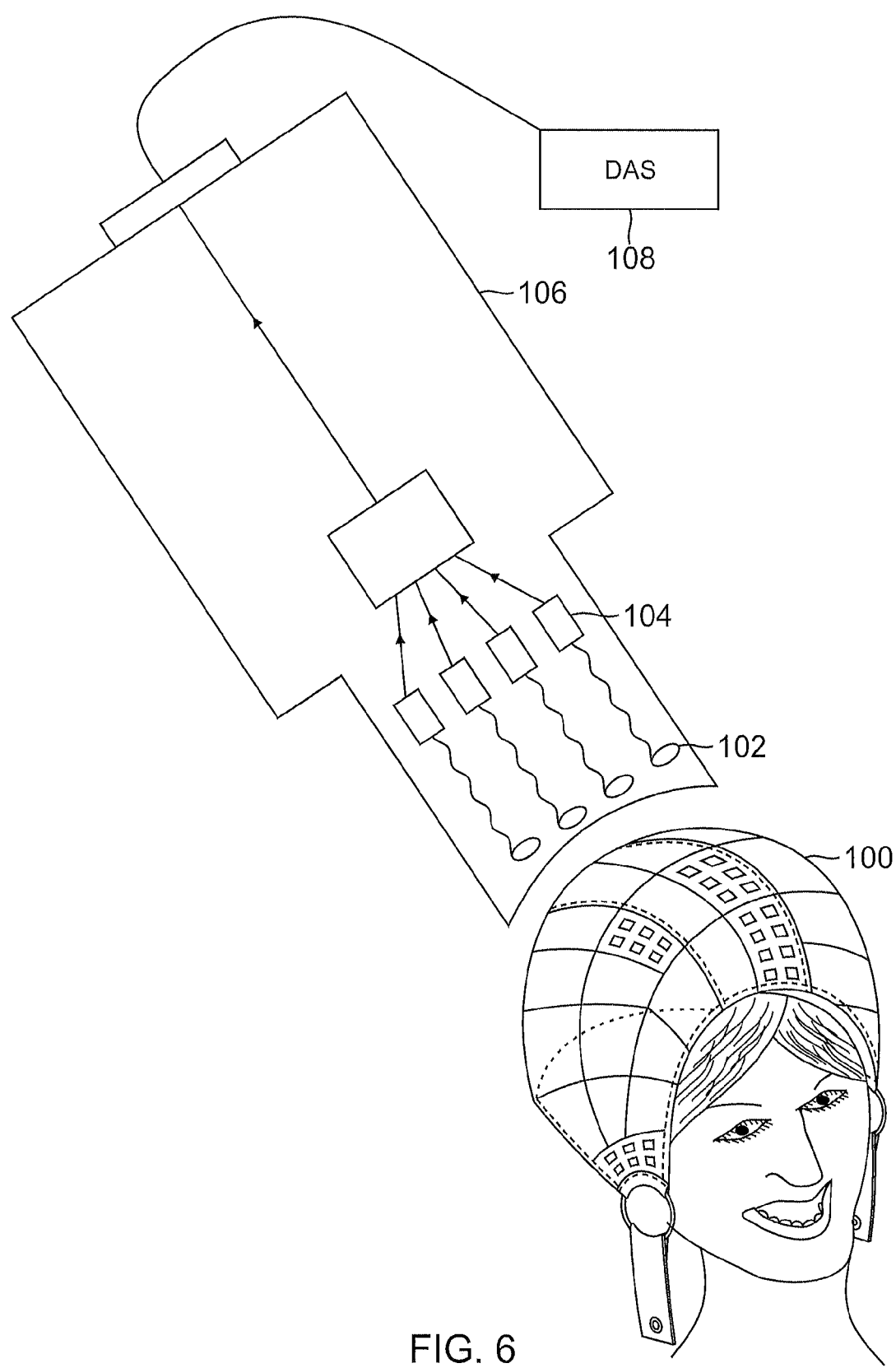
FIG. 6 is a schematic view of an apparatus which enables the enhanced detection of electric currents flowing in the brain of a human being through use of an array of primary source mirror modules as shown in FIG. 5, in accordance with an embodiment of the invention.

FIG. 6 shows a PRISM cap 100 made up of an array of PRISM modules on the head of a human subject, and a magnetic sensor 106 positioned over the cap to make magnetic measurements. The magnetic sensor utilizes pick-up coil antennae 102 to simultaneously and noninvasively detect the magnetic fields of the primary source currents flowing in the head of the subject and the magnetic fields of the secondary sources induced in the PRISMs within the modules. The signals picked up by the antennae are conveyed to superconducting amplifiers 104 and then to a data acquisition and processing system 108. By way of reiteration, prior to the development of the PRISM modules which are the subject of embodiments of the current invention, magnetic sensor 106 could only detect the portion of electrical currents within the brain of a human head which flow in a direction parallel to the surface of the head. The array of PRISM modules making up cap 100 now enables the sensor to also detect and measure the portion of electrical currents flowing within the brain in a direction perpendicular to the surface.

Figure 7:
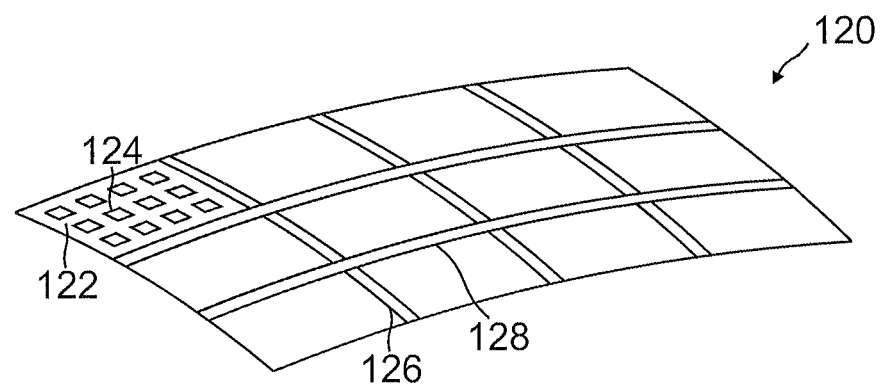
FIG. 7 shows a number of primary source mirror modules attached together to form a shape which conforms to the chest of a human being.

FIG. 7 shows an array of PRISM modules constructed using the same methods described above to fabricate a "blanket" of modules with an overall shape which conforms to or can be adjusted to fit to the chest of a human being. As with the PRISM module array cap described above, the same methods of fabricating modules of various shapes and attaching modules together is used to produce the blanket. In FIG. 7, one example of a blanket 120 is shown which is three modules wide by four modules long. In this case, each module 122 is rectangular, and each module contains a 4×3 rectangular array of PRISMs 124. The modules are attached to each other by their flanges 126, 128 using, for example, one of the attachment methods discussed above. In this case, selection of an attachment method which is robust under flexure is preferred to enable the entire blanket to readily adapt to the chests or backs of human bodies wherein measurements of the electric currents in the heart or spine is of interest. A similar blanket-like structure may be constructed to fit a human neck if the electric currents flowing in the neurological system of the upper spine are of interest. In these and similar applications, the array of PRISMs enables the simultaneous and noninvasive measurement of the primary magnetic fields produced by electric currents flowing within the sample below the "blanket" of PRISM modules and the secondary sources induced in the PRISMs within the "blanket" through the use of a suitable multichannel magnetometer.

Figure 8A:
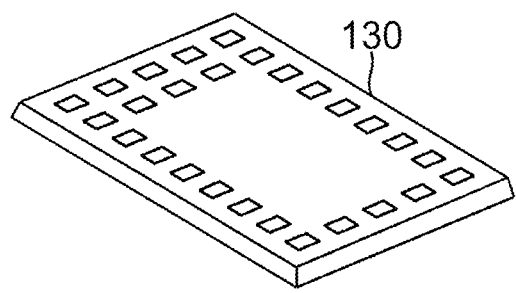
FIGS. 8a and 8b show a primary source mirror module with a flat conductive surface to be placed adjacent to a biological sample having a flat surface.
Figure 8B:
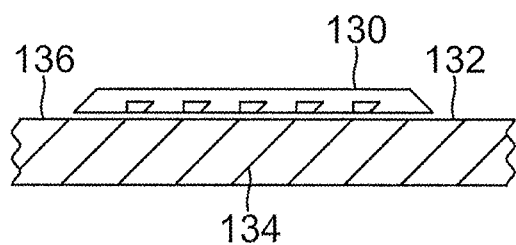

FIG. 8 shows a completely flat PRISM array 130 for use with biological sample 134 having flat surface 136 against which the flat conductive surface 132 of the PRISM array can be placed. This embodiment enables application of a PRISM array for the measurement of biomagnetic signals produced by small flat biological samples. Again in this application, the PRISM array enables the simultaneous measurement of secondary sources induced in any number of PRISMs within the array through use of a suitable magnetometer.

While particular embodiments of the present invention have been disclosed, it is to be understood that various different modifications and combinations are possible and are contemplated within the true spirit and scope of the disclosed embodiments. There is no intention, therefore, of limitations to the exact disclosures herein presented.

What is claimed is:

1. A module enabling improved noninvasive measurement of electric currents flowing in the body of a human being or animal or in other biological samples, the module comprising:
    an enclosure having two walls and an interior space, one wall being electrically conductive;
    an electrically conductive medium filling the interior space of the enclosure; and
    at least one electrically non-conductive solid body within the interior space and attached to the electrically conductive wall, the solid body having one flat surface adjacent to the electrically conductive wall wherein the angle between the flat surface and the electrically conductive wall is an acute angle greater than zero degrees.

2. The module of claim 1, wherein a plurality of electrically non-conductive solid bodies are attached to the electrically conductive wall, each solid body having one flat surface adjacent to the electrically conductive wall, wherein the angle between the flat surface and the electrically conductive wall is an acute angle greater than zero degrees.

3. The module of claim 1, wherein the enclosure has an external edge and a flange along a portion of the external edge.

4. The module of claim 1, wherein the electrically conductive medium is an electrically conductive gelatinous material.

5. The module of claim 1, wherein the electrically conductive medium is an electrically conductive liquid.

6. The module of claim 1, wherein the electrically non-conductive solid body is a rectangular solid having one flat side.

7. The module of claim 1, wherein the electrically non-conductive solid body is made from a material selected from the group comprising glass, quartz, sapphire, diamond, reinforced plastic, and non-reinforced plastic.

8. The module of claim 1, wherein the acute angle is 45 degrees.

9. The module of claim 2, wherein the acute angle for each solid body is 45 degrees.

10. The module of claim 1, wherein each electrically non-conductive solid body is a tetrahedron having a planar bottom surface and at least one planar triangular side, wherein the bottom surface lies against the electrically conductive wall and the triangular side is tilted at a 45 degree angle from the plane of the bottom surface.

11. The module of claim 1, wherein each electrically non-conductive solid body is a pentahedron having a flat bottom surface and a flat square surface, wherein the flat bottom surface lies against the electrically conductive wall and the flat square surface is tilted at a 45 degree angle from the plane of the flat bottom surface.

12. The module of claim 1, wherein each electrically non-conductive solid body is a hexahedron having a flat bottom surface and a flat square surface, wherein the flat bottom surface lies against the electrically conductive wall and the flat square surface is tilted at a 45 degree angle from the plane of the flat bottom surface.

13. The module of claim 1, wherein the electrically conductive wall comprises a semi-permeable membrane.

14. An array of modules enabling improved noninvasive measurement of electric currents flowing in a sample selected from the group comprising the body of a human being, the body of an animal, and another biological sample, the array comprising:
    a plurality of modules, each module comprising:
        an enclosure having two walls and an interior space, one wall being electrically conductive, the enclosure having an external edge and a flange along a portion of the external edge;
        an electrically conductive medium filling the interior space of the enclosure; and
        at least one electrically non-conductive solid body within the interior space and attached to the electrically conductive wall, the solid body having one flat surface adjacent to the electrically conductive wall wherein the angle between the flat surface and the electrically conductive wall is an acute angle greater than zero degrees;
    the flange of each module being attached to the flange of at least one other module.

15. The array of modules of claim 14, wherein attachment of the flanges of the modules is a stitching.

16. The array of modules of claim 14, wherein the attachment of the flanges is by means of an adhesive.

17. The array of modules of claim 14, wherein the attachment of the flanges is by means of a hook-and-loop system.

18. The array of modules of claim 14, wherein the array is in the form of a cap which is conformable to the shape of a human head.

19. The array of modules of claim 14, wherein the array is in the form of a blanket which is conformable to the shape of a portion of the human body.

20. The array of modules of claim 14, wherein the array is generally flat and conformable to the shape of a flat biological sample.

21. A method for enabling improved noninvasive measurement of electric currents flowing in a sample selected from the group comprising the body of a human being, the body of an animal, and another biological sample, the method comprising:
   placing an array of modules on the sample, the array of modules comprising:
      a plurality of modules, each module comprising:
         an envelope-shaped enclosure having two walls and an interior space, one wall being electrically conductive, the envelope-shaped enclosure having an external edge and a flange along a portion of the external edge;
         an electrically conductive medium filling the interior space of the enclosure; and
         at least one electrically non-conductive solid body within the interior space and attached to the electrically conductive wall, the solid body having one flat surface adjacent to the electrically conductive wall wherein the angle between the flat surface and the electrically conductive wall is an acute angle greater than zero degrees;
      the flange of each module being attached to the flange of at least one other module;
   placing a magnetometer adjacent to the sample so that the array of modules lies between the magnetometer and the sample; and
   measuring the magnetic field produced by the electric currents.

22. The method of claim 21, wherein the magnetometer employs superconducting quantum interference devices to measure the magnetic field.

23. The method of claim 22, wherein the magnetometer simultaneously measures the magnetic field over the entire array of modules.

24. The method of claim 21, wherein the array of modules forms of a cap which is conformable to the shape of a human head.

25. The method of claim 21, wherein the array is in the form of a blanket which is conformable to the shape of a portion of the human body.

26. The method of claim 21, wherein the array is in the form of a flat structure which is conformable to the shape of a flat biological sample.

* * * * *